US009406972B2

United States Patent
Shatunov et al.

(10) Patent No.: US 9,406,972 B2
(45) Date of Patent: Aug. 2, 2016

(54) FLAME RETARDANT MONOSUBSTITUTED PENTAFLUOROCYCLOTRIPHOSPHAZENE ELECTROLYTE ADDITIVE AND ELECTROLYTE INCLUDING THE SAME AND RECHARGEABLE LITHIUM BATTERY INCLUDING THE SAME

(71) Applicant: Samsung SDI Co., Ltd., Yongin-si (KR)

(72) Inventors: Pavel Shatunov, Yongin-si (KR);
Woo-Cheol Shin, Yongin-si (KR);
Makhmut Khasanov, Yongin-si (KR);
Denis Chernyshov, Yongin-si (KR);
Alexey Tereshchenko, Yongin-si (KR);
Vladimir Egorov, Yongin-si (KR)

(73) Assignee: Samsung SDI Co., Ltd., Gyeonggi-Do (KR)

( * ) Notice: Subject to any disclaimer, the term of this patent is extended or adjusted under 35 U.S.C. 154(b) by 218 days.

(21) Appl. No.: 13/720,028

(22) Filed: Dec. 19, 2012

(65) Prior Publication Data
US 2013/0295470 A1 Nov. 7, 2013

Related U.S. Application Data

(60) Provisional application No. 61/643,102, filed on May 4, 2012.

(51) Int. Cl.
*H01M 10/0567* (2010.01)
*H01M 10/056* (2010.01)
*C07F 9/6593* (2006.01)
*H01M 10/052* (2010.01)
*H01M 10/42* (2006.01)

(52) U.S. Cl.
CPC ......... *H01M 10/056* (2013.01); *C07F 9/65815* (2013.01); *H01M 10/052* (2013.01); *H01M 10/0567* (2013.01); *H01M 10/4235* (2013.01); *H01M 2300/0034* (2013.01); *Y02E 60/122* (2013.01)

(58) Field of Classification Search
CPC .................................................. H01M 10/0567
USPC .......................................................... 429/338
See application file for complete search history.

(56) References Cited

U.S. PATENT DOCUMENTS

2008/0153005 A1* 6/2008 Horikawa et al. ............. 429/314
2012/0219865 A1   8/2012 Kaneko et al.

FOREIGN PATENT DOCUMENTS

| CN | 101057355 A | 10/2007 |
|---|---|---|
| EP | 2 325 936 A1 | 5/2011 |
| GB | 1 388 430 | 3/1975 |
| JP | 2007-115583 A | 5/2007 |

(Continued)

OTHER PUBLICATIONS

T. Chivers et al., "A Convenient Route to Monosubstituted and Nongeminal Derivatives of Phosphonitrilic Fluorides," *Chemical Communications*, vol. 7, Dec. 31, 1969, p. 337.

(Continued)

*Primary Examiner* — Sean P Cullen
(74) *Attorney, Agent, or Firm* — Knobbe Martens Olson & Bear, LLP

(57) ABSTRACT

An electrolyte additive and electrolyte and lithium rechargeable battery including the electrolyte additive are provided. The electrolyte additive may be a monosubstituted pentafluorocyclotriphosphazene.

7 Claims, 1 Drawing Sheet

(56) References Cited

FOREIGN PATENT DOCUMENTS

| KR | 10-2005-0013144 A | 2/2005 |
| WO | WO 2011/052428 A1 | 5/2011 |
| WO | WO 2013/047342 A1 | 4/2013 |

OTHER PUBLICATIONS

European Extended Search Report dated Nov. 6, 2013 for European Patent Application No. EP 13 150 402.9, which claims priority from U.S. Appl. No. 61/643,102, filed May 4, 2012, and captioned U.S. Appl. No. 13/720,028.

Chivers et al., "Phosphonitrilic Derivatives. Part XIX. Dimethylaminofluorophosphonitriles and their Reactions with Hydrogen Halides as a Route to Monosubstituted and Non-geminal Derivatives of the Phosphonitrilic Fluorides," *J. Chem. Soc.* (A), 2324-2329 (1970).

Dalavi et al., "Nonflammable Electrolytes for Lithium-Ion Batteries Containing Dimethyl Methylphosphonate," *Journal of the Electrochemical Society*, 157 (10) A1113-1120 (2010).

Ding et al., "Effects of Tris(2,2,2-trifluoroethyl) Phosphate as a Flame-Retarding Cosolvent on Physiochemical Properties of Electrolytes of $LiPF_6$ in EC-PC-EMC of 3:3:4 Weight Ratios," *Journal of the Electrochemical Society*, 149 (11) A1489-A1498 (2002).

Hyung et al., "Flame-retardant additives for lithium-ion batteries," *Journal of Power Sources* 119-121 (2003) 383-387.

Niecke et al., "2.4.4.6.6-Pentalfluoro-1.3.5.2.4.6-triazaphosphor(V)inyl-(2)-amines and hydrazines ("Pentalfluorocyclotriphosphazo-amines and hydrazines")," *Chem. Ber.* 104, 3729-3729 (1971).

Niecke et al., "Äthylmercaptofluortriphosphazene," *Z. Naturforschung* 24b, 1187-1188 (1969).

Niecke et al., "Fluorocyclotriphosphazenes of the Type $P_3N_3F_5X$ (X=$CH_3$, $CHCH_2$, $SCH_3$, $SC_6H_5$, $OCH_3$, $OC_2H_5$, $OC_6H_5$)," *Z. Naturforschung* 26b, 366-367 (1971).

Ota et al., "Effect of cyclic phosphate additive in non-flammable electrolyte," *Journal of Power Sources* 119-121 (2003) 393-398.

Rivals et al., "Syntheses and Structures of Trilithium Cyclotriphosphazenates Equipped with 2-Halo-aryl Substitutents," *Z. Anorg. Allg. Chem.* 2003, 629, 139-146.

Wang et al., "Nonflammable Trimethyl Phosphate Solvent-Containing Electrolytes for Lithium-Ion Batteries," *Journal of the Electrochemical Society*, 148 (10) A1066-A1071 (2001).

Xiang et al., "Dimethyl methylphosphonate-based nonflammable electrolyte and high safety lithium-ion batteries," *Journal of Power Sources* 174 (2007) 335-341.

Xu et al., "An Attempt to Formulate Nonflammable Lithium Ion Electrolytes with Alkyl Phosphates and Phosphazenes," *Journal of the Electrochemical Society*, 149 (5) A622-A626 (2002).

Xu et al., "Nonflammable Electrolytes for Li-Ion Batteries Based on a Fluorinated Phosphate," *Journal of the Electrochemical Society*, 149 (8) A1079-A1082 (2002).

Xu et al., "Evaluation of Fluorinated Alkyl Phosphates as Flame Retardants in Electrolytes for Li-Ion Batteries, I. Physical and Electrochemical Properties," *Journal of the Electrochemical Society*, 150 (2) A161-A169 (2003).

Xu et al., "Evaluation of Fluorinated Alkyl Phosphates as Flame Retardants in Electrolytes for Li-Ion Batteries, II. Performance in Cell," *Journal of the Electrochemical Society*, 150 (2) A170-A175 (2003).

European Examination Report dated Mar. 10, 2016 for European Patent Application No. EP 13 150 402,9, which shares priority of U.S. Appl. No. 61/643,102, filed May 4, 2012, with subject U.S. Appl. No. 13/720,028.

Chinese Office Action dated Mar. 22, 2016 for Chinese Patent Application No. CN 201310159823.4, which shares priority of U.S. Appl. No. 61/643,102, filed May 4, 2012, with subject U.S. Appl. No. 13/720,028.

Pitina et al., "Synthesis of some substituted N'-isopropylidenoximinocyclotriphosphazenes," *Zh. Obshch, Khim.* 37, 2076-2080 (1967).

Pitina et al., "Synthesis of some substituted N'-isopropylidenoximinocyclotriphosphazenes," *Journal of General Chemistry of the USSR* [*translation of Zh, Obshch. Khim.*], 37, 1968-1971 (1967).

\* cited by examiner

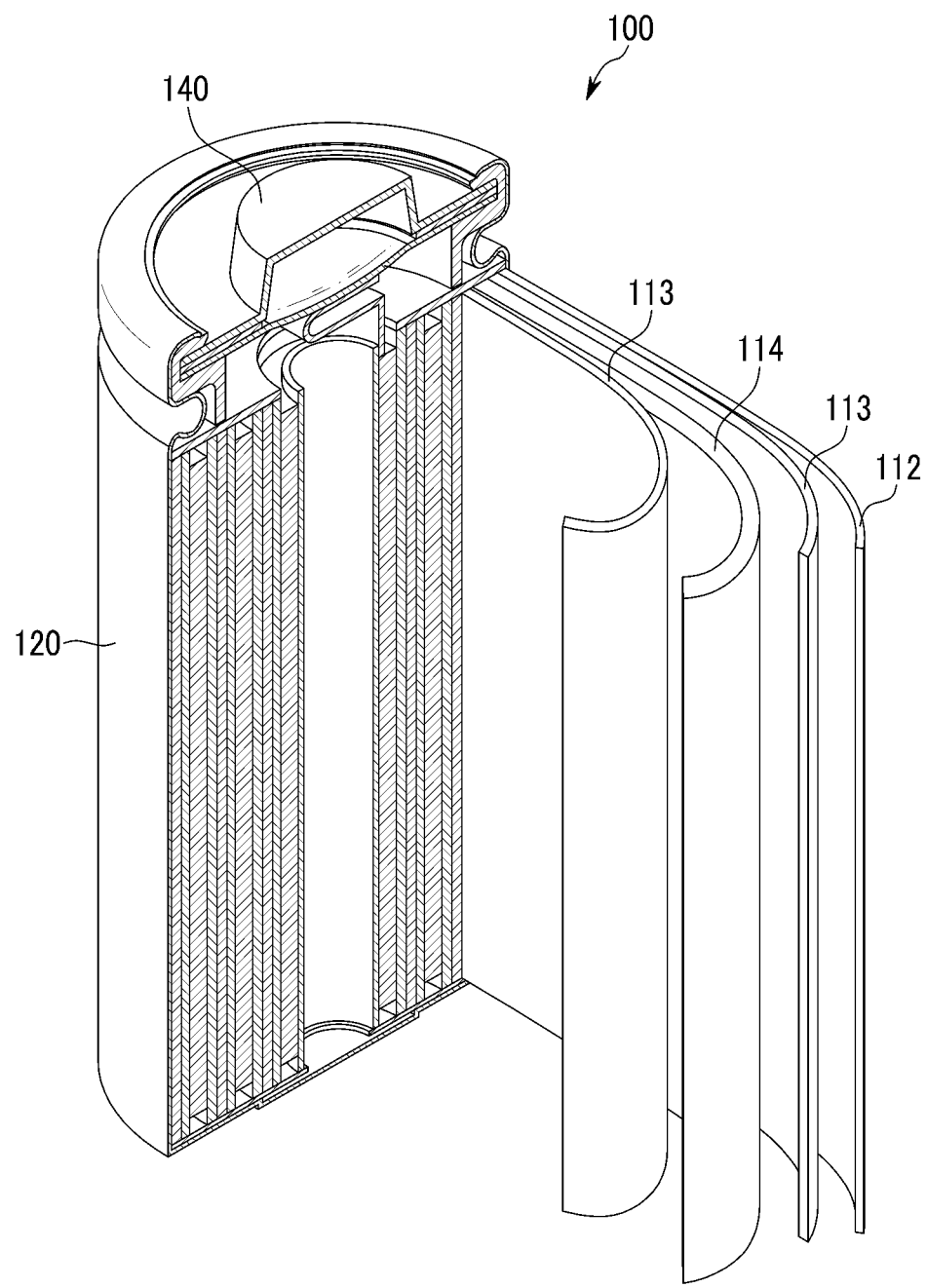

FLAME RETARDANT MONOSUBSTITUTED PENTAFLUOROCYCLOTRIPHOSPHAZENE ELECTROLYTE ADDITIVE AND ELECTROLYTE INCLUDING THE SAME AND RECHARGEABLE LITHIUM BATTERY INCLUDING THE SAME

CROSS-REFERENCE TO RELATED APPLICATION

This application claims priority under 35 U.S.C. §119(e) to U.S. Provisional Application No. 61/643,102 filed May 4, 2012, the disclosure of which is incorporated in its entirety herein by reference.

BACKGROUND

1. Field

This disclosure relates to an electrolyte additive, and an electrolyte and a rechargeable lithium battery including the same.

2. Description of the Related Technology

Batteries transform chemical energy generated from an electrochemical redox reaction into electrical energy. Such batteries are divided into a primary battery, which is not rechargeable and should be disposed after the energy of the battery is all consumed, and a rechargeable battery, which can be recharged many times based on a reversible transformation between chemical energy and electrical energy.

Recent developments in high-tech electronics have allowed electronic devices to become small and light in weight, which allows such devices to be portable. The demand for batteries with high energy density are increasing and research on lithium rechargeable batteries as a power source for such portable electronic devices is progressing.

A rechargeable lithium battery may be fabricated by injecting electrolyte into a battery cell. Such a rechargeable lithium battery includes a positive electrode including a positive active material capable of intercalating/deintercalating lithium, a negative electrode including a negative active material capable of intercalating/deintercalating lithium and an electrolyte.

An electrolyte typically includes an organic solvent in which a lithium salt is dissolved and may determine stability and performance of a rechargeable lithium battery. Particularly, stability is important in a large capacity rechargeable lithium battery.

SUMMARY

One embodiment provides an electrolyte additive being capable of maintaining performance while securing stability.

Another embodiment provides an electrolyte including the electrolyte additive. Yet another embodiment provides a rechargeable lithium battery including the electrolyte.

Some embodiments provide a compound of Chemical Formula 1:

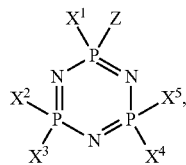

Chemical Formula 1 wherein, in Chemical Formula 1,
$X^1$ may be a halogen atom or $X^{1A}$;
$X^2$ may be a halogen atom or $X^{1A}$;
$X^3$ may be a halogen atom or $X^{1A}$;
$X^4$ may be a halogen atom or $X^{1A}$;
$X^5$ may be a halogen atom or $X^{1A}$;
$X^{1A}$ may be a C1 to C30 alkyl group, a C3 to C30 cycloalkyl group, an aryl group, a substituted or unsubstituted C3 to C30 cycloalkenyl group, a substituted C7 to C20 arylalkyl group, a C1 to C20 heteroalkyl group, a C2 to C30 heterocycloalkyl group, a heteroaryl group, a C2 to C30 alkenyl group, a C2 to C30 alkynyl group, or a C1 to C20 aldehyde group, each substituted with one or more halogen atoms;
Z may be —$NR^1R^2$;
$R^1$ may be a substituted or unsubstituted C1 to C30 alkyl group, a substituted or unsubstituted C3 to C30 cycloalkyl group, a substituted or unsubstituted C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a substituted or unsubstituted C1 to C20 aldehyde group; and
$R^2$ may be a substituted or unsubstituted C1 to C30 alkyl group, a substituted or unsubstituted C3 to C30 cycloalkyl group, a substituted or unsubstituted C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a substituted or unsubstituted C1 to C20 aldehyde group.

Some embodiments provide an electrolyte for a rechargeable lithium battery, comprising an electrolyte additive component represented by Chemical Formula 1:

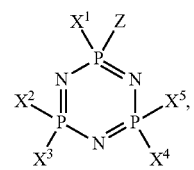

Chemical Formula 1 wherein, in Chemical Formula 1,
$X^1$ may be a halogen atom or $X^{1A}$;
$X^2$ may be a halogen atom or $X^{1A}$;
$X^3$ may be a halogen atom or $X^{1A}$;
$X^4$ may be a halogen atom or $X^{1A}$;
$X^5$ may be a halogen atom or $X^{1A}$;
$X^{1A}$ may be a C1 to C30 alkyl group, a C3 to C30 cycloalkyl group, an aryl group, a substituted or unsubstituted C3 to C30 cycloalkenyl group, a substituted C7 to C20 arylalkyl group, a C1 to C20 heteroalkyl group, a C2 to C30 heterocycloalkyl group, a heteroaryl group, a C2 to C30 alkenyl group, a C2 to C30 alkynyl group, or a C1 to C20 aldehyde group, each substituted with one or more halogen atoms;

Z may be —NR$^1$R$^2$;

R$^1$ may be a substituted or unsubstituted C1 to C30 alkyl group, a substituted or unsubstituted C3 to C30 cycloalkyl group, a substituted or unsubstituted C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a substituted or unsubstituted C1 to C20 aldehyde group;

R$^2$ may be a substituted or unsubstituted C1 to C30 alkyl group, a substituted or unsubstituted C3 to C30 cycloalkyl group, a substituted or unsubstituted C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a substituted or unsubstituted C1 to C20 aldehyde group;

a lithium salt; and an organic solvent component.

Some embodiments provide a rechargeable lithium battery comprising a negative electrode including a negative active material; a positive electrode including a positive active material; and, an electrolyte as disclosed and described herein. In certain embodiments, the electrolyte may include a compound of Chemical Formula 1.

In certain embodiments, in Chemical Formula 1, at least one of X$^1$, X$^2$, X$^3$, X$^4$, and X$^5$ may be a halogen atom. In certain embodiments, in Chemical Formula 1, at least one of X$^1$, X$^2$, X$^3$, X$^4$, and X$^5$ may be a fluorine.

In certain embodiments, in Chemical Formula 1,

X$^1$ may be a halogen atom; X$^2$ may be a halogen atom; X$^3$ may be a halogen atom; X$^4$ may be a halogen atom; X$^5$ may be a halogen atom; R$^1$ may be a substituted or unsubstituted C1 to C30 alkyl group, or a substituted or unsubstituted C3 to C30 cycloalkyl group; and R$^2$ may be a substituted or unsubstituted C1 to C30 alkyl group, or a substituted or unsubstituted C3 to C30 cycloalkyl group.

In certain embodiments, the electrolyte additive may be monosubstituted pentafluorocyclotriphosphazene.

In certain embodiments, the lithium salt may include LiPF$_6$, LiBF$_4$, LiSbF$_6$, LiAsF$_6$, LiN(SO$_2$C$_2$F$_5$)$_2$, LiN(SO$_2$CF$_3$)$_2$, LiN(SO$_3$C$_2$F$_5$)$_2$, LiC$_4$F$_9$SO$_3$, LiClO$_4$, LiAlO$_2$, LiAlCl$_4$, LiN(SO$_2$C$_x$F$_{2x+1}$)(SO$_2$C$_y$F$_{2y+1}$) wherein x and y are natural numbers of 1 to 20, respectively, LiCl, LiI, LiB(C$_2$O$_4$)$_2$ (lithium bis(oxalato) borate), or one or more combinations thereof.

In certain embodiments, the electrolyte may include from about 0.01% to about 50% by volume of the electrolyte additive component based on the total volume of the electrolyte.

In certain embodiments, the electrolyte may include from about 5% to about 20% by volume of the electrolyte additive component based on the total volume of the electrolyte.

In certain embodiments, the organic solvent component may include one or more compounds selected from the group consisting of diethyl carbonate (DEC), dipropyl carbonate (DPC), methylpropyl carbonate (MPC), ethylpropyl carbonate (EPC), methylethyl carbonate (MEC), ethylmethyl carbonate (EMC), propylene carbonate (PC), and butylene carbonate (BC).

In certain embodiments, the compound of Formula 1 may be

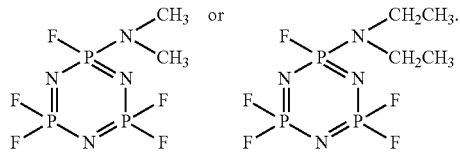 [SMILES: CN(C)P1(F)=NP(F)(F)=NP(F)(F)=N1 ; CCN(CC)P1(F)=NP(F)(F)=NP(F)(F)=N1]

Some embodiments provide an electrolyte for a rechargeable lithium battery including a lithium salt, a non-aqueous organic solvent, and an electrolyte additive as disclosed and described herein.

In certain embodiments, provided is a rechargeable lithium battery including a lithium salt wherein the lithium salt includes LiPF$_6$, LiBF$_4$, LiSbF$_6$, LiAsF$_6$, LiN(SO$_2$C$_2$F$_5$)$_2$, LiN(SO$_2$CF$_3$)$_2$, LiN(SO$_3$C$_2$F$_5$)$_2$, LiC$_4$F$_9$SO$_3$, LiClO$_4$, LiAlO$_2$, LiAlCl$_4$, LiN(SO$_2$C$_x$F$_{2x+1}$)(SO$_2$C$_y$F$_{2y+1}$) wherein x and y are natural numbers of 1 to 20, respectively, LiCl, LiI, LiB(C$_2$O$_4$)$_2$ (lithium bis(oxalato) borate), or one or more combinations thereof.

A battery including an electrolyte as disclosed and described herein may maintain performance while securing stability due to improvement of flame retardancy.

BRIEF DESCRIPTION OF THE DRAWINGS

FIG. 1 is a schematic view showing a rechargeable lithium battery according to one embodiment, and

DESCRIPTION OF SYMBOLS

100: Lithium rechargeable battery
112: negative electrode
113: separator
114: positive electrode
120: battery case
140: sealing member

DETAILED DESCRIPTION

Exemplary embodiments will hereinafter be described in detail. However, these embodiments are exemplary, and this disclosure is not limited thereto.

As those skilled in the art would realize, the described embodiments may be modified in various different ways, all without departing from the spirit or scope of the present disclosure.

As used herein, when a definition is not otherwise provided, the term 'substituted' may refer to one substituted with a substitutent selected from a halogen atom (F, Br, Cl, or I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when a definition is not otherwise provided, the term 'hetero' may refer to a group including 1 to 3 heteroatoms selected from, N (nitrogen), O (oxygen), S (sulfur), and P (phosphorus).

In certain embodiments, the electrolyte additive may be a compound represented by the following Chemical Formula 1.

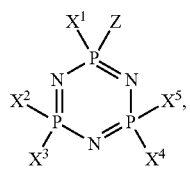

Chemical Formula 1 wherein, in Chemical Formula 1,
$X^1$ may be a halogen atom or $X^{1A}$;
$X^2$ may be a halogen atom or $X^{1A}$;
$X^3$ may be a halogen atom or $X^{1A}$;
$X^4$ may be a halogen atom or $X^{1A}$;
$X^5$ may be a halogen atom or $X^{1A}$;
$X^{1A}$ may be a C1 to C30 alkyl group, a C3 to C30 cycloalkyl group, an aryl group, a substituted or unsubstituted C3 to C30 cycloalkenyl group, a substituted C7 to C20 arylalkyl group, a C1 to C20 heteroalkyl group, a C2 to C30 heterocycloalkyl group, a heteroaryl group, a C2 to C30 alkenyl group, a C2 to C30 alkynyl group, or a C1 to C20 aldehyde group, each substituted with one or more halogen atoms;
Z may be $-NR^1R^2$;
$R^1$ may be a substituted or unsubstituted C1 to C30 alkyl group, a substituted or unsubstituted C3 to C30 cycloalkyl group, a substituted or unsubstituted C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a substituted or unsubstituted C1 to C20 aldehyde group; and
$R^2$ may be a substituted or unsubstituted C1 to C30 alkyl group, a substituted or unsubstituted C3 to C30 cycloalkyl group, a substituted or unsubstituted C1 to C30 haloalkyl group, a substituted or unsubstituted C6 to C30 aryl group, a substituted or unsubstituted C6 to C30 halogenated aryl group, a substituted or unsubstituted C3 to C30 cycloalkenyl group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C2 to C30 alkenyl group, a substituted or unsubstituted C2 to C30 alkynyl group, or a substituted or unsubstituted C1 to C20 aldehyde group.

In certain embodiments, the electrolyte additive is a cyclotriphosphazene derivative, including three phosphorus atoms (P) and three nitrogen atoms (N) that form a ring. In certain embodiments, two of the three phosphorus atoms (P) are connected with a halogen atom or halogen-containing group and the other phosphorus atom (P) is connected with a halogen atom or halogen-containing group and an amino group.

In certain embodiments, the electrolyte additive represented by the Chemical Formula 1 may be monosubstituted halogenated cyclotriphospazene.

In certain embodiments, $X^1$ to $X^5$ of the Chemical Formula 1 may be fluorine to provide monosubstituted pentafluorocyclotriphosphazene.

In certain embodiments, $R^1$ to $R^3$ of the Chemical Formula 1 may be each independently a substituted or unsubstituted C1 to C30 alkyl group, a substituted or unsubstituted C1 to C30 haloalkyl group, or a combination thereof, and Z may be a dialkylamino group.

In certain embodiments, the electrolyte additive represented by Chemical Formula 1 may be included in the electrolyte so as to improve flame retardancy of the electrolyte while not affecting the performance of a battery.

In certain embodiments, the electrolyte for a rechargeable lithium battery may include an electrolyte additive represented by the Chemical Formula 1, a non-aqueous organic solvent, and a lithium salt.

In certain embodiments, the electrolyte additive may be included in an amount of about 0.01 to about 50 volume % based on the total amount of the electrolyte. In certain embodiments, flame retardancy of the electrolyte may be improved while not deteriorating the performance of a battery with the electrolyte additive included in an amount of about 0.01 to about 50 volume % based on the total amount of the electrolyte. In certain embodiments, the additive may be included in an amount of about 5 to 20 volume %. In certain embodiments, the additive may be included in an amount of about 10 to 15 volume %.

In certain embodiments, the non-aqueous organic solvent plays a role of transmitting ions taking part in the electrochemical reaction of a battery.

In certain embodiments, the non-aqueous organic solvent may include a carbonate-based, ester-based, ether-based, ketone-based, alcohol-based, or aprotic solvent.

In certain embodiments, the carbonate-based solvent may include dimethyl carbonate (DMC), diethyl carbonate (DEC), dipropyl carbonate (DPC), methylpropyl carbonate (MPC), ethylpropyl carbonate (EPC), ethylmethyl carbonate (EMC), ethylene carbonate (EC), propylene carbonate (PC), butylene carbonate (BC), and the like. In certain embodiments, the ester-based solvent may include methyl acetate, ethyl acetate, n-propyl acetate, dimethylacetate, methylpropionate, ethylpropionate, gamma-butyrolactone, decanolide, gamma-valerolactone, mevalonolactone, caprolactone, and the like.

In certain embodiments, the ether-based solvent may include dibutyl ether, tetraglyme, diglyme, dimethoxyethane, 2-methyltetrahydrofuran, tetrahydrofuran and the like, and the ketone-based solvent may include cyclohexanone, and the like.

In certain embodiments, the alcohol-based solvent may include ethanol, isopropyl alcohol, and the like. The aprotic solvent include nitriles such as R—CN (wherein R is a C2 to C20 linear, branched, or cyclic hydrocarbon group, and may include a double bond, an aromatic ring, or an ether bond), amides such as dimethylformamide, dimethylacetamide, dioxolanes such as 1,3-dioxolane, sulfolanes, and the like.

In certain embodiments, the non-aqueous organic solvent may be used singularly or in a mixture. When the organic solvent is used in a mixture, its mixture ratio can be controlled in accordance with desirable performance of a battery as disclosed and described herein.

In certain embodiments, the carbonate-based solvent may include a mixture of a cyclic carbonate and a linear carbonate. In certain embodiments, the cyclic carbonate and the linear carbonate are mixed together in a volume ratio of about 1:1 to about 1:9, which may enhance performance of an electrolyte. In certain embodiments, the non-aqueous organic solvent may be prepared by further adding the aromatic hydrocarbon-based solvent to the carbonate-based solvent. In certain embodiments, the carbonate-based solvent and the aromatic hydrocarbon-based solvent may be mixed together in a volume ratio of about 1:1 to about 30:1. In certain embodiments, the aromatic hydrocarbon-based organic solvent may be selected from the group consisting of benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and a combination thereof.

In certain embodiments, the lithium salt may be dissolved in the non-aqueous organic solvent which may improve lithium ion transfer between positive and negative electrodes. In certain embodiments, the lithium salt includes one or more of $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_2$, $LiAlCl_4$, $LiN(C_xF_{2x-1}SO_2)(C_yF_{2y-1}SO_2)$ (wherein, x and y are natural numbers, of 1 to 20, respectively), LiCl, and LiI In certain embodiments, the lithium salt may be used at a concentration of about 0.1 to about 2.0M. When the lithium salt is included within the above concentration range, it may electrolyte performance and lithium ion mobility due to optimal electrolyte conductivity and viscosity.

In certain embodiments, the electrolyte may further include an additive selected from lithium bis(oxalate)borate (LiBOB), lithium bis(salicylato)borate (LiBSB), and a combination thereof. In certain embodiments, the lithium bis(oxalate)borate (LiBOB) and/or lithium bis(salicylato)borate (LiBSB) may improve thermal stability of an electrolyte and cycle capability of a battery.

Hereinafter, a rechargeable lithium battery according one embodiment is described referring to FIG. 1.

FIG. 1 is a schematic view of a rechargeable lithium battery according to one embodiment.

Referring to FIG. 1, a rechargeable lithium battery 100 according to one embodiment includes a battery cell including a positive electrode 114, a negative electrode 112 facing the positive electrode 114, a separator 113 interposed between the positive electrode 114 and negative electrode 112, and an electrolyte for a rechargeable lithium battery (not shown) impregnating the positive electrode 114, negative electrode 112, and separator 113, a battery case 120 including the battery cell, and a sealing member 140 sealing the battery case 120.

In certain embodiments, the rechargeable lithium battery 100 may be fabricated by sequentially laminating a negative electrode 112, a positive electrode 114, and a separator 113, spirally winding them, and housing the spiral-wound product in a battery case 120.

In certain embodiments, the negative electrode 112 may include a current collector and a negative active material layer disposed on at least one side of the current collector.

In certain embodiments, the current collector may include a copper foil, a nickel foil, a stainless steel foil, a titanium foil, a nickel foam, a copper foam, a polymer substrate coated with a conductive metal, or a combination thereof.

In certain embodiments, the negative active material layer may include a negative active material, a binder and optionally, a conductive material.

In certain embodiments, the negative active material may include a material that reversibly intercalates/deintercalates lithium ions, a lithium metal, a lithium metal alloy, a material being capable of doping and dedoping lithium, or transition metal oxide.

In certain embodiments, the material that reversibly intercalates/deintercalates lithium ions includes a carbon material. In certain embodiments, the carbon material may be any generally-used carbon-based negative active material in a lithium ion rechargeable battery. Examples of the carbon material include crystalline carbon, amorphous carbon, and a mixture thereof. In certain embodiments, the crystalline carbon may be non-shaped or sheet, flake, spherical, or fiber shaped natural graphite or artificial graphite. In certain embodiments, the amorphous carbon may be a soft carbon (carbon obtained by sintering at a low temperature), a hard carbon, mesophase pitch carbonization products, fired coke, and the like.

Examples of the lithium metal alloy include, but are not limited to, lithium and Na, K, Rb, Cs, Fr, Be, Mg, Ca, Sr, Si, Sb, Pb, In, Zn, Ba, Ra, Ge, Al, or Sn.

In certain embodiments, the material being capable of doping and dedoping lithium may include Si, $SiO_x$ (0<x<2), a Si—C composite, a Si-Q alloy (wherein Q is an alkali metal, an alkaline-earth metal, Group 13 to Group 16 elements, a transition element, a rare earth element, or a combination thereof, and is not Si), Sn, $SnO_2$, a Sn—C composite, Sn—R (wherein R is an alkali metal, an alkaline-earth metal, Group 13 to Group 16 elements, a transition element, a rare earth element, or a combination thereof, and not Sn), and the lile. In certain embodiments, the elements Q and R may include Mg, Ca, Sr, Ba, Ra, Sc, Y, Ti, Zr, Hf, Rf, V, Nb, Ta, Cr, Mo, W, Tc, Re, Fe, Pb, Ru, Os, Rh, Ir, Pd, Pt, Cu, Ag, Au, Zn, Cd, B, Al, Ga, Sn, In, Ti, Ge, P, As, Sb, Bi, S, Se, Te, Po, or a combination thereof.

In certain embodiments, the transition metal oxide may include vanadium oxide, lithium vanadium oxide, and the like.

In certain embodiments, the binder may improve properties of binding active material particles with one another and a negative active material with a current collector. Examples of the binder include, but are not limited to, polyvinylalcohol, carboxylmethylcellulose, hydroxypropylcellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like.

In certain embodiments, the conductive material may improve electrical conductivity of a negative electrode. Any electrically conductive material can be used as a conductive agent, unless it causes a chemical change. Examples of the conductive material include, but are not limited to, a carbon-based material such as natural graphite, artificial graphite, carbon black, acetylene black, ketjen black, a carbon fiber, and the like; a metal-based material of a metal powder or a metal fiber including copper, nickel, aluminum, silver, and the like; a conductive polymer such as a polyphenylene derivative, and the like; or a mixture thereof.

In certain embodiments, the positive electrode 114 may include a current collector and a positive active material layer disposed on the current collector.

In certain embodiments, the current collector may be an Al, but is not limited thereto.

In certain embodiments, the positive active material layer includes a positive active material, a binder, and optionally a conductive material.

In certain embodiments, the positive active material includes lithiated intercalation compounds that reversibly intercalate and deintercalate lithium ions. In certain embodiments, the positive active material may include a composite oxide including at least one selected from the group consisting of cobalt, manganese, and nickel, as well as lithium.

Specific examples may be the compounds represented by the following chemical formulae:

$Li_aA_{1-b}R_bD_2$ (wherein, in the preceding Chemical Formula, $0.90 \le a \le 1.8$ and $0 \le b \le 0.5$);
$Li_aE_{1-b}R_bO_{2-c}D_c$ (wherein, in the preceding Chemical Formula, $0.90 \le a \le 1.8$, $0 \le b \le 0.5$ and $0 \le c \le 0.05$);
$LiE_{2-b}R_bO_{4-c}D_c$ (wherein, in the preceding Chemical Formula, $0 \le b \le 0.5$, $0 \le c \le 0.05$);
$Li_aNi_{1-b-c}Co_bR_cD_\alpha$ (wherein, in the preceding Chemical Formula, $0.90 \le a \le 1.8$, $0 \le b \le 0.5$, $0 \le c \le 0.05$ and $0 < \alpha \le 2$);
$Li_aNi_{1-b-c}Co_bR_cO_{2-\alpha}Z_\alpha$ (wherein, in the preceding Chemical Formula, $0.90 \le a \le 1.8$, $0 \le b \le 0.5$, $0 \le c \le 0.05$ and $0 < \alpha < 2$);
$Li_aNi_{1-b-c}Co_bR_cO_{2-\alpha}Z_2$ (wherein, in the preceding Chemical Formula, $0.90 \le a \le 1.8$, $0 \le b \le 0.5$, $0 \le c \le 0.05$ and $0 \le a \le 2$);
$Li_aNi_{1-b-c}Mn_bR_cD_\alpha$ (wherein, in the preceding Chemical Formula, $0.90 \le a \le 1.8$, $0 \le b \le 0.5$, $0 \le c \le 0.05$ and $0 \le \alpha \le 2$);
$Li_aNi_{1-b-c}Mn_bR_cO_{2-\alpha}Z_\alpha$ (wherein, in the preceding Chemical Formula, $0.90 \le a \le 1.8$, $0 \le b \le 0.5$, $0 \le c \le 0.05$ and $0 < \alpha < 2$);
$Li_aNi_{1-b-c}Mn_bR_cO_{2-\alpha}Z_2$ (wherein, in the preceding Chemical Formula, $0.90 \le a \le 1.8$, $0 \le b \le 0.5$, $0 \le c \le 0.05$ and $0 < \alpha < 2$);
$Li_aNi_bE_cG_dO_2$ (wherein, in the preceding Chemical Formula, $0.90 \le a \le 1.8$, $0 \le b \le 0.9$, $0 \le c \le 0.5$ and $0.001 \le d \le 0.1$);
$Li_aNi_bCo_cMn_dGeO_2$ (wherein, in the preceding Chemical Formula, $0.90 \le a \le 1.8$, $0 \le b \le 0.9$, $0 \le c \le 0.5$, $0 \le d \le 0.5$ and $0.001 \le e \le 0.1$);
$Li_aNiG_bO_2$ (wherein, in the preceding Chemical Formula, $0.90 \le a \le 1.8$ and $0.001 \le b \le 0.1$);
$Li_aCoG_bO_2$ (wherein, in the preceding Chemical Formula, $0.90 \le a \le 1.8$ and $0.001 \le b \le 0.1$);
$Li_aMnG_bO_2$ (wherein, in the preceding Chemical Formula, $0.90 \le a \le 1.8$ and $0.001 \le b \le 0.1$);
$Li_aMn_2G_bO_4$ (wherein, in the preceding Chemical Formula, $0.90 \le a \le 1.8$ and $0.001 \le b \le 0.1$);
$QO_2$; $QS_2$; $LiQS_2$; $V_2O_5$; $LiV_2O_5$; $LiTO_2$; $LiNiVO_4$;
$Li_{(3-f)}J_2(PO_4)_3$ ($0 \le f \le 2$); $Li_{(3-f)}Fe_2(PO_4)_3$ ($0 \le f \le 2$); and $LiFePO_4$.

In the above Chemical Formulae, A may be Ni, Co, Mn, or a combination thereof; R may be Al, Ni, Co, Mn, Cr, Fe, Mg, Sr, V, a rare earth element, or a combination thereof; D may be O (oxygen), F (fluorine), S (sulfur), P (phosphorus), or a combination thereof; E may be Co, Mn, or a combination thereof; Z may be F (fluorine), S (sulfur), P (phosphorus), or a combination thereof; G may be Al, Cr, Mn, Fe, Mg, La, Ce, Sr, V, or a combination thereof; Q may be Ti, Mo, Mn, or a combination thereof; T may be Cr, V, Fe, Sc, Y, or a combination thereof; and J may be V, Cr, Mn, Co, Ni, Cu, or a combination thereof.

In certain embodiments, the positive active material may be a compound with the coating layer on the surface or a mixture of the active material and a compound with the coating layer thereon. In certain embodiments, the coating layer may include at least one coating element compound selected from the group consisting of an oxide and a hydroxide of the coating element, an oxyhydroxide of the coating element, an oxycarbonate of the coating element, and a hydroxycarbonate of the coating element. In certain embodiments, the compound for the coating layer may be either amorphous or crystalline. In certain embodiments, the coating element included in the coating layer may be Mg, Al, Co, K, Na, Ca, Si, Ti, V, Sn, Ge, Ga, B, As, Zr, or a mixture thereof. In certain embodiments, the coating process may include any conventional processes unless it causes any side effects on the properties of the positive active material (e.g., spray coating, immersing), well known to those who have ordinary skill in this art.

In certain embodiments, the binder improves binding properties of the positive active material particles to one another and to a current collector. Examples of the binder include polyvinylalcohol, carboxylmethylcellulose, hydroxypropylcellulose, diacetylcellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like, but is not limited thereto.

In certain embodiments, the conductive material improves electrical conductivity of a negative electrode. Any electrically conductive material can be used as a conductive agent unless it causes a chemical change. Examples of the conductive material include natural graphite, artificial graphite, carbon black, acetylene black, ketjen black, a carbon fiber, a metal powder or a metal fiber including copper, nickel, aluminum, silver, and the like. A conductive material such as a polyphenylene derivative and the like may be mixed.

In certain embodiments, the negative and positive electrodes may be fabricated in a method of preparing an active material composition by mixing the active material and a binder, and optionally a conductive material, and coating the active material composition on a current collector. In certain embodiments, the solvent may include N-methylpyrrolidone and the like but is not limited thereto. The electrode manufacturing method is known to those of skill in the art.

In certain embodiments, the separator 113 separates the positive electrode 114 and negative electrode 112 and provides a path for transferring lithium ions. In certain embodiments, the separator 113 may be any separator that is generally used in a lithium ion battery. In certain embodiments, the separator may have low resistance against electrolyte ions and excellent moisturizing capability of an electrolyte. For example, the separator may be selected from a glass fiber, polyester, polyethylene, polypropylene, polytetrafluoroethylene (PTFE), or a combination thereof and may have a non-woven fabric type or a fabric type. For example, a polyolefin-based polymer separator such as polyethylene, polypropylene, and the like is used for a lithium ion battery, a separator coated with a ceramic component or a polymer material may be used to secure heat resistance or mechanical strength. In certain embodiments, the separator may have a singular layer. In certain embodiments, the separator may have multi-layers.

In certain embodiments, the rechargeable lithium battery may be classified as a lithium ion battery, a lithium ion polymer battery, and a lithium polymer battery according to the presence of a separator and the kind of an electrolyte used therein. In certain embodiments, the rechargeable lithium battery may have a variety of shapes and sizes and thus, may include a cylindrical, prismatic, coin, or pouch-type battery and a thin film type or a bulky type in size.

In certain embodiments, the electrolyte may be the electrolyte as disclosed and described herein.

The following examples illustrate the aspects of present embodiments described above, in more detail. These examples, however, should not in any sense be interpreted as limiting the scope of the present embodiments.

Preparation of Electrolyte Additive

Synthesis Example 1

A mixture of hexafluorocyclotriphosphazene (15.66 g, 63 mmol) dissolved in diethyl ether (79 mL) was prepared. The mixture was cooled to 0° C. and then treated with a 2M dimethylamine solution (63 mL, 126 mmol) and stirred for 1 hour. The resulting mixture was agitated overnight at room temperature to provide a mixture with a solid precipitate. The liquid was decanted from the precipitate and the precipitate was washed with ether. Subsequently, combined organic portions (decanted portion and from washings) were evaporated to provide an oil. The residual oil was distilled twice to afford 8.86 g of a compound represented by the following Chemical Formula 1A. The yield was 51.3%. Boiling point is 94-95° C./175 Torr.

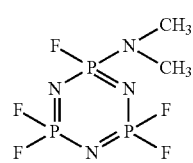

Chemical Formula 1A

Synthesis Example 2

A mixture of hexafluorocyclotriphosphazene (14.94 g, 60 mmol) dissolved in diethyl ether (100 mL) was prepared. The mixture was cooled to 0° C. and then treated with a diethylamine (8.78 g, 120 mmol) and stirred for 1 hour. The resulting mixture was agitated overnight at room temperature to provide a mixture with a solid precipitate. The liquid was decanted from the precipitate and the precipitate was washed with ether. Subsequently, combined organic portions (decanted portion and from washings) were evaporated to provide an oil. The residual oil was distilled twice to afford 5.56 g of a compound represented by the following Chemical Formula 1B. The yield was 30.7%. Boiling point is 125-128° C./175 Torr.

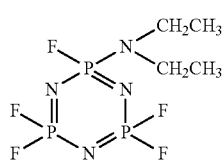

Chemical Formula 1B

Comparative Synthesis Example 1

A solution of propylamine (5.91 g, 100 mmol) in diethyl ether (100 mL) was added dropwise to a solution of hexafluorocyclotriphosphazene (12.45 g, 50 mmol) in diethyl ether (100 mL) at 0° C. for 2 hours. The mixture was stirred overnight at room temperature. The solution was decanted from a sticky precipitate and subsequently was washed with ether. The combined ether solutions were washed with water and dried over anhydrous magnesium sulfate. Subsequently, diethyl ether was evaporated and a residual oil was distilled twice to obtain 5.86 g of a compound represented by the following Chemical Formula 2. The yield was 40.7%. Boiling point is 80° C./23 Torr.

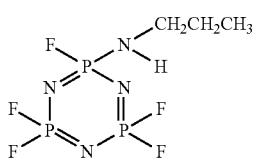

Chemical Formula 2

Comparative Synthesis Example 2

1.66 g (8.8%) of a compound represented by the following Chemical Formula 3 was obtained through two-stage fractional distillation of a residual material remained after distilling off the mono-substituted product of Synthesis Example 1. Boiling point is 90-92° C./10 Torr.

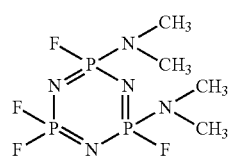

Chemical Formula 3

Preparation of Electrolyte

Example 1

An electrolyte for a rechargeable lithium battery was prepared by adding 1.3M LiPF$_6$ lithium salt to a mixed solvent of ethylene carbonate (EC), ethylmethylcarbonate (EMC) and dimethylcarbonate (DMC) in a ratio of 3/4/3 (v/v/v), and adding 10 volume % of the additive obtained in Synthesis Example 1 to the mixture.

Example 2

An electrolyte for a rechargeable lithium battery was prepared according to the same method as Example 1, except that the additive obtained in Synthesis Example 2 was used instead of the additive obtained in Synthesis Example 1.

Comparative Example 1

An electrolyte for a rechargeable lithium battery was prepared according to the same method as Example 1, except that no additive was included.

Comparative Example 2

An electrolyte for a rechargeable lithium battery was prepared according to the same method as Example 1, except that the additive obtained in Comparative Synthesis Example 1 was used instead of the additive obtained in Synthesis Example 1.

Comparative Example 3

An electrolyte for a rechargeable lithium battery was prepared according to the same method as Example 1, except that the additive obtained in Comparative Synthesis Example 2 was used instead of the additive obtained in Synthesis Example 1.

Evaluation of Flame Retardancy Using Glass Fiber Filter

Evaluation 1: Flame Retardancy

Flame retardance of the electrolytes according to Examples 1 and 2 and Comparative Examples 1 to 3 was evaluated. The flame retardance of each sample was evaluated by getting glass fiber filters (WHATMAN®, GF/C, 4.7 cm, 1.2 μm) wet with the electrolytes according to Examples 1 and 2 and Comparative Examples 1 to 3, igniting the glass fiber filters, and measuring the time that the glass fiber filters were burnt. The time may be represented by self-extinguishing time (SET) and it is denoted with time (s/mL) per unit volume.

The result was shown in Table 1.

TABLE 1

|  | SET (s/mL) |
| --- | --- |
| Example 1 | 14.6 |
| Example 2 | 17 |
| Comparative Example 1 | 18.3 |
| Comparative Example 2 | 15.6 |
| Comparative Example 3 | 18 |

The data in Table 1 indicates that the electrolytes according to Examples 1 and 2 had shorter self-extinguishing time than the electrolytes according to Comparative Examples 1 to 3. The electrolytes according to Examples 1 and 2 had superior flame retardancy to the electrolytes according to Comparative Examples 1 to 3.

Evaluation of Flame Retardancy Using Coin Cell

Each of the electrolytes (250 mL) prepared according to Examples 1 and 2 and Comparative Examples 1 to 3 was poured onto the bottom surface of coin cell case 2032 (Hohsen Corp., Osaka, Japan), respectively, and ignited, and its burning time was measured. The time may be represented by self-extinguishing time (SET), and denoted with time per unit weight (s/g).

The results are as shown in Table 2.

TABLE 2

|  | SET (s/g) |
| --- | --- |
| Example 1 | 0 |
| Example 2 | 0 |
| Comparative Example 1 | 99 |
| Comparative Example 2 | 78 |
| Comparative Example 3 | 79 |

Referring to Table 2, whereas the electrolytes according to Examples 1 and 2 were not ignited in the coin cells and showed excellent flame retardancy, the electrolytes according to Comparative Examples 1 to 3 maintained the ignition state for longer than one minute and showed poor flame retardancy.

Evaluation 2: Evaluation of Cycle Capability

Rechargeable lithium battery cells were fabricated using the electrolytes according to Examples 1 and 2 and Comparative Example 1. Herein, 92 wt % of NCM433-NCM111 (1:4 wt/wt; Nickel-Cobalt-Manganese), 4 wt % of Denka black, and 4 wt % of polyvinylidenefluoride (PVdF, Solef6020) were used as a positive electrode, and a graphite negative active material coated with alumina was used as a negative electrode.

Rechargeable lithium battery cells including the electrolytes according to Examples 1 and 2 and Comparative Example 1 were charged and discharged 100 times at 25° C. with 1C (operation voltage: 2.7V to 4.2V), and discharge capacity for each cycle was measured.

The capacity retentions after 100 cycles were as shown in Table 3.

TABLE 3

|  | Capacity retention (%) |
| --- | --- |
| Example 1 | 91 |
| Example 2 | 95 |
| Comparative Example 1 | 92 |

It may be seen from Table 3 that after 100 cycles, the rechargeable lithium battery cells using the electrolytes from Examples 1 and 2 acquired a similar capacity retention to that of the rechargeable lithium battery cell using the electrolyte according to Comparative Example 1, which was the electrolyte including no additive.

It may be understood that the electrolytes from Examples 1 and 2 do not deteriorate the performance of a battery cell while improving flame retardancy.

While this disclosure has been described in connection with what is presently considered to be practical exemplary embodiments, it is to be understood that the invention is not limited to the disclosed embodiments and is intended to cover various modifications and equivalent arrangements included within the spirit and scope of the appended claims. Therefore, the aforementioned embodiments should be understood to be exemplary but not limiting this disclosure in any way.

What is claimed is:

1. An electrolyte for a rechargeable battery, consisting of: an electrolyte additive component of Chemical Formula 1:

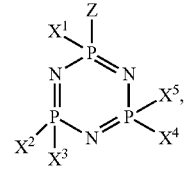

Chemical Formula 1 wherein, in Chemical Formula 1,
X$^1$ is a fluorine;
X$^2$ is a fluorine;
X$^3$ is a fluorine;
X$^4$ is a fluorine
X$^5$ is a fluorine;
Z is —NR$^1$R$^2$;
R$^1$ is an unsubstituted C1 to C30 alkyl group;
R$^2$ is an unsubstituted C1 to C30 alkyl group;
a lithium salt; and
an organic solvent component, wherein an amount of the electrolyte additive component is between about 0.01% and 15% by volume based on the total volume of the electrolyte.

2. The electrolyte for a rechargeable lithium battery of claim 1, wherein the electrolyte includes from between about 5% and 15% by volume of the electrolyte additive component based on the total volume of the electrolyte.

3. The electrolyte for a rechargeable lithium battery of claim 1, wherein the organic solvent component includes one or more compounds selected from the group consisting of diethyl carbonate (DEC), dipropyl carbonate (DPC), methylpropyl carbonate (MPC), ethylpropyl carbonate (EPC), methylethyl carbonate (MEC), ethylmethyl carbonate (EMC), propylene carbonate (PC), and butylene carbonate (BC).

4. The electrolyte for a rechargeable lithium battery of claim 1, wherein the compound of Formula 1 is

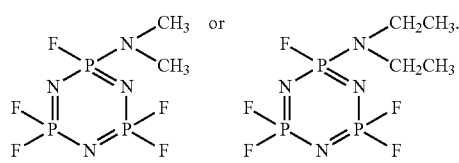 [SMILES: CN(C)P1(F)=NP(F)(F)=NP(F)(F)=N1 ; CCN(CC)P1(F)=NP(F)(F)=NP(F)(F)=N1]

5. A rechargeable lithium battery comprising
a negative electrode including a negative active material;
a positive electrode including a positive active material; and,
the electrolyte of claim 1.

6. The rechargeable lithium battery of claim 5, wherein the compound of Formula 1 is

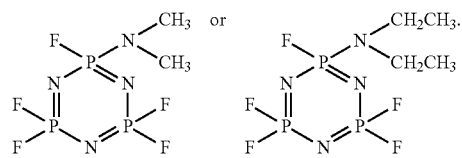

7. The rechargeable lithium battery of claim 6, wherein the lithium salt comprises $LiPF_6$, $LiBF_4$, $LiSbF_6$, $LiAsF_6$, $LiN(SO_2C_2F_5)_2$, $LiN(SO_2CF_3)_2$, $LiN(SO_3C_2F_5)_2$, $LiC_4F_9SO_3$, $LiClO_4$, $LiAlO_2$, $LiAlCl_4$, $LiN(SO_2C_xF_{2x+1})(SO_2C_yF_{2y+1})$ wherein x and y are natural numbers of 1 to 20, respectively, LiCl, LiI, $LiB(C_2O_4)_2$ (lithium bis(oxalato)borate), or one or more combinations thereof.

* * * * *